(12) United States Patent
Blume et al.

(10) Patent No.: US 9,745,330 B2
(45) Date of Patent: Aug. 29, 2017

(54) OLIGOMERIC ORGANOSILANES, THE PRODUCTION THEREOF AND THE USE THEREOF IN RUBBER MIXTURES

(71) Applicants: Anke Blume, Weilerswist (DE); Ralph Moser, Freiburg i. Br. (DE); Sebastian Rosenstingl, Rheinfelden (DE)

(72) Inventors: Anke Blume, Weilerswist (DE); Ralph Moser, Freiburg i. Br. (DE); Sebastian Rosenstingl, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/036,994

(22) PCT Filed: Jan. 8, 2015

(86) PCT No.: PCT/EP2015/050242
§ 371 (c)(1),
(2) Date: May 16, 2016

(87) PCT Pub. No.: WO2015/107000
PCT Pub. Date: Jul. 23, 2015

(65) Prior Publication Data
US 2016/0289251 A1  Oct. 6, 2016

(30) Foreign Application Priority Data
Jan. 15, 2014 (DE) .................. 10 2014 200 563

(51) Int. Cl.
| | | |
|---|---|---|
| C07F 7/18 | (2006.01) |
| C08K 5/548 | (2006.01) |
| C08L 83/12 | (2006.01) |
| C08G 77/04 | (2006.01) |
| C08G 77/28 | (2006.01) |
| C08G 77/392 | (2006.01) |
| C08G 77/46 | (2006.01) |

(52) U.S. Cl.
CPC ............ *C07F 7/1804* (2013.01); *C08K 5/548* (2013.01); *C08L 83/12* (2013.01); *C08G 77/045* (2013.01); *C08G 77/28* (2013.01); *C08G 77/392* (2013.01); *C08G 77/46* (2013.01)

(58) Field of Classification Search
CPC .............................. C07F 7/1804; C08K 5/548
See application file for complete search history.

(56) References Cited

U.S. PATENT DOCUMENTS

| | | |
|---|---|---|
| 5,827,912 A | 10/1998 | Scholl |
| 6,005,027 A | 12/1999 | Guillet et al. |
| 6,180,076 B1 | 1/2001 | Uhrlandt et al. |

(Continued)

FOREIGN PATENT DOCUMENTS

| | | |
|---|---|---|
| DE | 100 41 163 A1 | 3/2002 |
| DE | 10 2004 049 427 A1 | 4/2006 |

(Continued)

OTHER PUBLICATIONS

International Search Report and Written Opinion issued Feb. 17, 2015 in PCT/EP2015/050242 filed Jan. 8, 2015 (with English translation of the Search Report).

(Continued)

*Primary Examiner* — Robert Harlan
(74) *Attorney, Agent, or Firm* — Oblon, McClelland, Maier & Neustadt, L.L.P.

(57) ABSTRACT

The present invention relates to oligomeric organosilanes containing at least two different structural units within a molecule, selected from the structural units A, B, C and D joined in any desired linear, branched or cyclic arrangement,

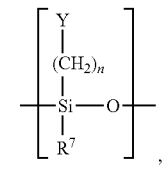

A

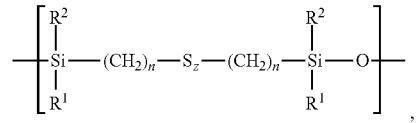

B

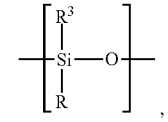

C

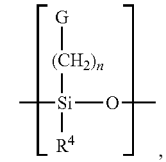

D wherein at least one R, $R^1$, $R^2$, $R^3$, $R^4$ or $R^7$ group is an alkyl polyether group —O—($R^5$—O)$_m$—$R^6$, to the preparation thereof and to the use thereof in rubber mixtures.

21 Claims, No Drawings

(56) References Cited

U.S. PATENT DOCUMENTS

| | | | |
|---|---|---|---|
| 6,331,605 B1 * | 12/2001 | Lunginsland | C08G 77/48 523/213 |
| 7,566,433 B2 | 7/2009 | Stenzel et al. | |
| 8,597,425 B2 | 12/2013 | Stenzel et al. | |
| 8,658,816 B2 | 2/2014 | Wehmeier et al. | |
| 2003/0109614 A1 | 6/2003 | Luginsland et al. | |
| 2003/0180245 A1 | 9/2003 | Gotsche et al. | |
| 2007/0203274 A1 | 8/2007 | Korth et al. | |
| 2009/0030162 A1 | 1/2009 | Mueh et al. | |
| 2013/0251616 A1 | 9/2013 | Stenzel et al. | |
| 2016/0289251 A1 | 10/2016 | Blume et al. | |
| 2016/0326374 A1 | 11/2016 | Blume et al. | |

FOREIGN PATENT DOCUMENTS

| | | |
|---|---|---|
| EP | 0 748 839 A1 | 12/1996 |
| EP | 0 964 021 A2 | 12/1999 |
| EP | 0 964 021 A3 | 12/1999 |
| EP | 1 273 613 A2 | 1/2003 |
| EP | 1 273 613 A3 | 1/2003 |
| EP | 1 829 922 A1 | 9/2007 |
| JP | 2002-47416 | 2/2002 |
| JP | 2002-147890 | 5/2002 |
| WO | WO 2006/037380 A1 | 4/2006 |

OTHER PUBLICATIONS

Search Report issued Feb. 11, 2014 in German Patent Application No. 10 2014-200-563.9.

* cited by examiner

OLIGOMERIC ORGANOSILANES, THE PRODUCTION THEREOF AND THE USE THEREOF IN RUBBER MIXTURES

This application is a National Stage of PCT/EP2015/050242, which was filed on Jan. 8, 2015. This application is based upon and claims the benefit of priority to German Application No. 10 2014 200 563.9, which was filed on Jan. 15, 2014.

The present invention relates to oligomeric organosilanes, to a process for preparation thereof and to the use thereof in rubber mixtures.

It is known that sulphur-containing organosilicon compounds such as 3-mercaptopropyltrimethoxysilane or bis(3-[triethoxysilyl]propyl)tetrasulphane can be used as a silane adhesion promoter or reinforcing additive in rubber mixtures with oxidic fillers, including for tyre treads and other parts of automobile tyres (DE 2 141 159 DE 2 212 239, U.S. Pat. No. 3,978,103, U.S. Pat. No. 4,048,206).

EP 0 784 072 A1 discloses rubber mixtures based on at least one elastomer with silica as a filler and a reinforcing additive which is prepared by blending or as an in situ reaction product from at least one functional polyorganosiloxane compound, and which contain a functional organosilane as a further constituent. Monomeric units used are especially 3-mercaptopropyltrialkoxysilanes or bis(trialkoxysilylpropyl)tetrasulphanes, each of which bear 3 and 6 alkoxy substituents respectively.

In addition, EP 0964021 discloses oligomeric organosilane polysulphanes which are not polycondensed to give a solid, and which contain the structural units A and/or B and/or C in any linear, branched or cyclic arrangement

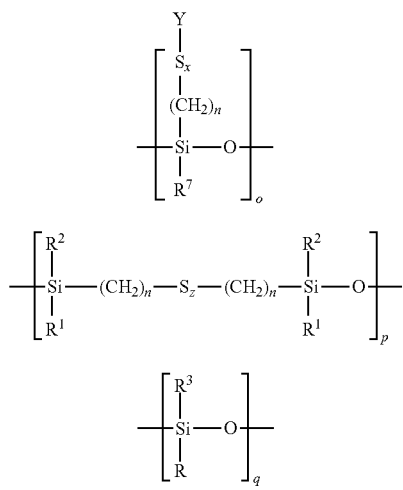

WO 2006/037380, EP 0997489 and EP 1273613 likewise disclose oligomeric organosilanes.

Disadvantages of the known oligo-/polysiloxanes are poor processability and poor tear resistance.

It is an object of the present invention to provide oligomeric organosilanes having improved processability and/or tear resistance.

The invention provides oligomeric organosilanes containing at least two different structural units within a molecule, selected from the structural units A, B, C and D joined in any desired linear, branched or cyclic arrangement,

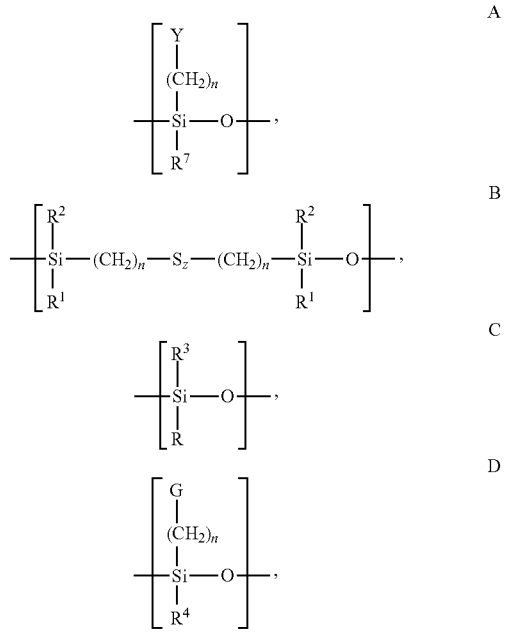

where Y=H, F, Cl, Br, I, SCN, SH, $-S_x-(CH_2)_n SiRR^1R^2$ or $-N(R^8)_2$, $R^8$ is the same or different and is H, $(C_1-C_{16})$alkyl, preferably $C_4$-alkyl, $-(CH_2)_2NH_2$, $-(CH_2)_2NH-(CH_2)_2NH_2$ or $-(CH_2)_2N[(CH_2)_2NH_2]_2$, with n=1-8, preferably n=2 or 3, G=H, F, Cl, Br, I, SCN, SH, $-S_x-(CH_2)_nSiRR^1R^2$ or $-N(R^8)_2$, with G different from Y, R, $R^1$, $R^2$, $R^3$, $R^4$, $R^7$ are each independently OH, $(C_1-C_{16})$alkyl, preferably methyl or ethyl, $(C_2-C_{16})$alkenyl, preferably $C_2$-alkenyl, $(C_6-C_{14})$ aryl, $(C_1-C_4)$alkoxy, preferably methoxy or ethoxy, an $OSiR^1R^2R^3$ group or an alkyl polyether group $-O-(R^5-O)_m-R^6$, where $R^5$ is the same or different and is a branched or unbranched, saturated or unsaturated, aliphatic divalent C1-C30 hydrocarbon group, preferably $-(CH_2)_2-$, $-(CH_2)_3-$ or $-(CH_2C(CH_3)H)-$, m on average is 1 to 30, preferably 3 to 8, more preferably 5, and $R^6$ is an unsubstituted or substituted, branched or unbranched $C_1-C_{30}$ alkyl group, preferably a $C_{11}-C_{19}$ alkyl group, $C_2-C_{30}$ alkenyl, preferably a $C_2$ alkenyl group, a $C_6-C_{14}$ aryl group, or a $C_7-C_{40}$ aralkyl group, x on statistical average is 1-6, preferably 2-4, z on statistical average is 1-6, preferably 2-4, which are characterized in that at least one R, $R^1$, $R^2$, $R^3$, $R^4$ or $R^7$ group is an alkyl polyether group $-O-(R^5-O)_m-R^6$.

The alkyl polyether group may preferably be $-O-(CH_2CH_2-O)_m-R^6$, more preferably $-O-(CH_2CH_2-O)_5-R^6$, most preferably $-O-(CH_2CH_2-O)_5-C_{13}H_{27}$.

The relative molar mass, measured by GPC, of the inventive oligomeric organosilanes in relation to a standard consisting of a mixture of siloxanes of vinyltrimethoxysilane, may be between 400 and 100 000 g/mol, preferably between 450 and 50 000 g/mol, more preferably between 600 and 10 000 g/mol.

The oligomeric organosilane may contain the structural units A and B and C, where $R^7$ is an alkyl polyether group $-O-(R^5-O)_m-R^6$, preferably with $R^5=-CH_2CH_2-$, m=5 and $R^6=-C_{13}H_{27}$. It may be the case here that, in the structural unit A, n=3, Y=SH, in the structural unit B, $R^1$=ethoxy or alkyl polyether group —O—$(R^5$—O$)_m$—$R^6$, $R^2$=ethoxy or alkyl polyether group —O—$(R^5$—O$)_m$—$R^6$, n=3, z=2-4, and in the structural unit C, R=phenyl, propyl or octyl and $R^3$=ethoxy or alkyl polyether group —O—$(R^5$—O$)_m$—$R^6$. The molar ratio of the molar proportion of the structural unit A to the sum total of the molar proportions of the structural units B and C may be greater than one.

The oligomeric organosilane may contain the structural units A and B, where $R^7$ is an alkyl polyether group —O—$(R^5$—O$)_m$—$R^6$, preferably with $R^5$=—CH$_2$CH$_2$—, m=5 and $R^6$=—C$_{13}$H$_{27}$. It may be the case here that, in the structural unit A, n=3, Y=SH, and in the structural unit B, $R^1$=ethoxy or alkyl polyether group —O—$(R^5$—O$)_m$—$R^6$, $R^2$=ethoxy or alkyl polyether group —O—$(R^5$—O$)_m$—$R^6$, n=3, z=2-4. The molar ratio of the molar proportion of the structural unit A to the molar proportion of the structural unit B may be greater than one.

The oligomeric organosilane may contain the structural units A and C, where $R^7$ is an alkyl polyether group —O—$(R^5$—O$)_m$—$R^6$, preferably with $R^5$=—CH$_2$CH$_2$—, m=5 and $R^6$=—C$_{13}$H$_{27}$. It may be the case here that, in the structural unit A, n=3, Y=SH, and in the structural unit C, R=phenyl, propyl or octyl and $R^3$=ethoxy or alkyl polyether group —O—$(R^5$—O$)_m$—$R^6$. The molar ratio of the molar proportion of the structural unit A to the molar proportion of the structural unit C may be greater than one.

The oligomeric organosilane may contain the structural units A and C and D, where $R^7$ is an alkyl polyether group —O—$(R^5$—O$)_m$—$R^6$, preferably with $R^5$=—CH$_2$CH$_2$—, m=5 and $R^6$=—C$_{13}$H$_{27}$. It may be the case here that, in the structural unit A, n=3, Y=SH, in the structural unit C, R=phenyl, propyl or octyl and $R^3$=ethoxy or alkyl polyether group —O—$(R^5$—O$)_m$—$R^6$, and in the structural unit D, G=Cl or NH$_2$, n=3, $R^4$=ethoxy or alkyl polyether group —O—$(R^5$—O$)_m$—$R^6$. The molar ratio of the molar proportion of the structural unit A to the sum total of the molar proportions of the structural units C and D may be greater than one.

The oligomeric organosilane may contain the structural units A and D, where $R^7$ is an alkyl polyether group —O—$(R^5$—O$)_m$—$R^6$, preferably with $R^5$=—CH$_2$CH$_2$—, m=5 and $R^6$=—C$_{13}$H$_{27}$. It may be the case here that, in the structural unit A, n=3, Y=SH, and in the structural unit D, G=Cl or NH$_2$, n=3, $R^4$=ethoxy or alkyl polyether group —O—$(R^5$—O$)_m$—$R^6$. The molar ratio of the molar proportion of the structural unit A to the molar proportion of the structural unit D may be greater than one.

These inventive oligomeric organosilanes may be cyclic via Y, branched or linear.

The inventive compounds may either be in the form of an individual compound having a defined molecular weight or in the form of an oligomer mixture having a molecular weight distribution.

The molar ratio of the alkyl polyether group —O—$(R^5$—O$)_m$—$R^6$ to silicon in the oligomeric organosilane may be >0 and <=2.0, preferably >0.1 and <=1.0. The molar ratio of the alkyl polyether group —O—$(R^5$—O$)_m$—$R^6$ to silicon can be ascertained via the molar proportion of the alkyl polyether group —O—$(R^5$—O$)_m$—$R^6$ and the molar proportion of silicon. The molar proportion of the alkyl polyether group —O—$(R^5$—O$)_m$—$R^6$ can be determined by a $^{13}$C NMR spectroscopy method known to those skilled in the art using an internal standard. The internal standard may be dimethyl terephthalate, naphthalene, or further internal standards for NMR spectroscopy known to those skilled in the art. The molar proportion of silicon can be ascertained with the aid of a method known to those skilled in the art for determining the Si content (for example ASTM 6740).

The present invention further provides a process for preparing the inventive oligomeric organosilanes, which is characterized in that, in a first process step, the compounds of the formula I-IV

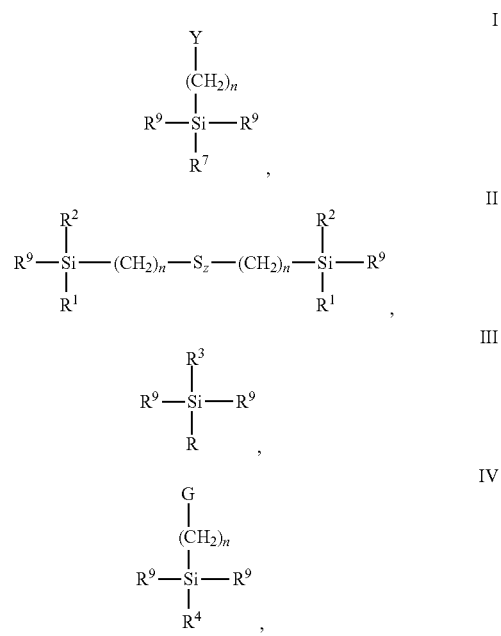

are oligomerized/polymerized according to the molar ratio in the presence of water at temperatures of 0-150° C., preferably of 20-130° C., more preferably 80-120° C., where Y, G, R, $R^1$, $R^2$, $R^3$, $R^4$, $R^5$, $R^6$, $R^7$, $R^8$, n, m, u, x and z are each as defined above, and $R^9$ is H, F, Cl, Br, I, (C$_1$-C$_{16}$) alkoxy, preferably methoxy or ethoxy, and, in a second process step, reacted with an alkyl polyether alcohol of the formula HO—$(R^5$—O$)_m$—$R^6$.

The process according to the invention, in the first and second process steps, can be conducted in the presence of a catalyst. In this case, the catalysts in the first and second process steps may be the same or different. The catalyst can be added here in catalytic or stoichiometric amounts. In this context, all kinds of acidic, basic or nucleophilic catalysts which are known to those skilled in the art from the SOLGEL chemistry of alkoxysilanes (see, for example, R. Corriu, D. Leclercq, Angew. Chem. 1996, 108, 1524-1540) are also suitable for the oligomerization in the context of the invention. It is unimportant here whether the catalysts are in the same phase as the reaction solution (homogeneous catalysis) or are in the form of solids (heterogeneous catalysis) and are removed after the reaction has ended.

Preference is given to conducting homogeneous catalysis with a Lewis acid, for example tetrabutyl orthotitanate, or by nucleophilic methods with ammonium fluoride, or by heterogeneous methods with aluminium oxide. Basic catalysis can be effected, for example, with an organic base such as triethylamine, tetramethylpiperidine, tributylamine or pyridine, or with an inorganic base such as NaOH, KOH, Ca(OH)$_2$, Na$_2$CO$_3$, K$_2$CO$_3$, CaCO$_3$, CaO, NaHCO$_3$, KHCO$_3$ or alkoxides such as NaOCH$_3$ or NaOC$_2$H$_5$. Nucleophilic catalysis can be accomplished with any desired fluorides, for example ammonium fluoride, sodium fluoride, potassium fluoride, or any desired tetraalkylammonium fluorides such as tetrabutylammonium fluoride. Acidic catalysis can be effected with dilute aqueous mineral acids or solutions of Lewis acids in water. Catalysis can preferably be effected with dilute aqueous HCl or sulphuric acid, using 0.1 mol % of catalyst based on the amount of silane used.

Very preferably, the catalyst used may be tetrabutyl orthotitanate, KOH, NaOH, ammonium fluoride or HCl.

Especially preferably, HCl may be used as catalyst in the first process step, and tetrabutyl orthotitanate in the second process step.

The process according to the invention can be performed in the presence of a solvent.

The oligomerization/polymerization reaction, in the case of addition of water, is effected with elimination of alcohol, hydrogen halide or hydrogen, and can be conducted here in substance or in an inert organic solvent or mixtures thereof, for example in an aromatic solvent such as chlorobenzene, a halogenated hydrocarbon such as chloroform, methylene chloride, an ether such as diisopropyl ether, tert-butyl methyl ether, tetrahydrofuran or diethyl ether, acetonitrile or carboxylic esters, for example ethyl acetate, methyl acetate or isopropyl acetate, an alcohol, for example methanol, ethanol, n-propanol, i-propanol, n-butanol, sec-butanol or tert-butanol. Preferred solvents here are ethanol or ethyl acetate.

The second process step can be conducted without further addition of a solvent.

The compounds of the formula I may, for example, be 3-mercaptopropyltrimethoxysilane, 3-mercaptopropyltriethoxysilane, bis(3-[triethoxysilyl]propyl)disulphane, bis(3-[triethoxysilyl]propyl)trisulphane, bis(3-[triethoxysilyl]propyl)tetrasulphane, 3-thiocyanatopropyltrimethoxysilane, 3-thiocyanatopropyltriethoxysilane, 3-aminopropyltrimethoxysilane, 3-aminopropyltriethoxysilane,

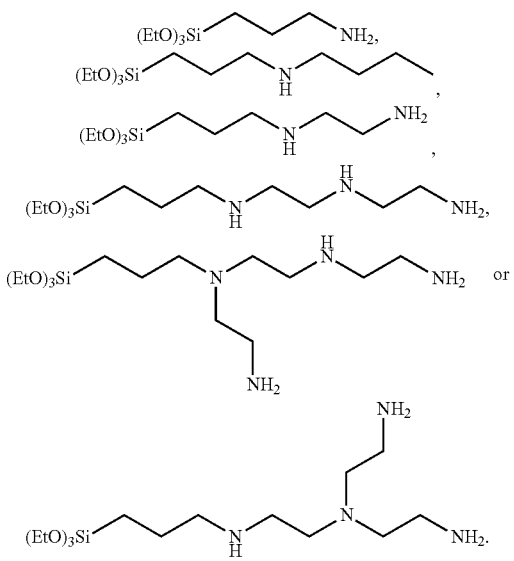

The compounds of the formula II may, for example, be bis(3-[triethoxysilyl]propyl)disulphane, bis(3-[triethoxysilyl]propyl)trisulphane or bis(3-[triethoxysilyl]propyl)tetrasulphane.

The compounds of the formula III may, for example, be methyltrimethoxysilane, methyltriethoxysilane, phenyltrimethoxysilane, phenyltriethoxysilane, propyltrimethoxysilane, propyltriethoxysilane, octyltrimethoxysilane, octyltriethoxysilane, hexadecyltrimethoxysilane, hexadecyltriethoxysilane, dimethyldimethoxysilane, dimethyldiethoxysilane or dichlorodimethylsilane.

The compounds of the formula IV may, for example, be 3-mercaptopropyltrimethoxysilane, 3-mercaptopropyltriethoxysilane, bis(3-[triethoxysilyl]propyl)disulphane, bis(3-[triethoxysilyl]propyl)trisulphane, bis(3-[triethoxysilyl]propyl)tetrasulphane, 3-thiocyanatopropyltrimethoxysilane, 3-thiocyanatopropyltriethoxysilane, 3-chloropropyltrimethoxysilane, 3-chloropropyltriethoxysilane, 3-aminopropyltrimethoxysilane, 3-aminopropyltriethoxysilane,

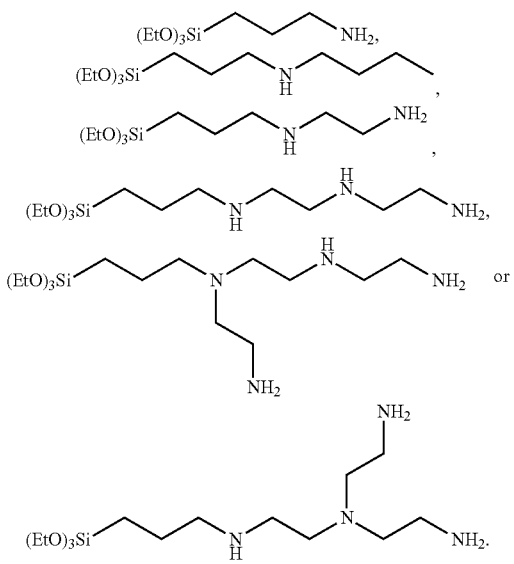

On completion of reaction, the volatile constituents can be removed in a manner known to those skilled in the art, preferably by distillation. The catalyst can be deactivated, preferably by neutralization, or removed, preferably by filtration.

The invention further provides for the use of the inventive organosilanes in rubber mixtures.

The invention further provides rubber mixtures comprising the inventive oligomeric organosilanes. The inventive rubber mixtures can be used for production of shaped bodies, especially pneumatic tyres or tyre treads.

The inventive rubber mixtures may comprise rubber, filler, preferably precipitated silica, optionally further rubber auxiliaries, and at least one oligomeric organosilane. The oligomeric organosilanes can be used in amounts of 0.1 to 15% by weight, based on the amount of the rubber used.

The use of the inventive oligomeric organosilanes in rubber blending processes distinctly reduces the unpleasant alcohol release because of the pre-condensation that has already taken place. Compared to the usual mode of operation, for example by simple use of bis(3-[triethoxysilyl]propyl)tetrasulphane (TESPT) as adhesion promoter, evolution of alcohol is reduced during the blending operation.

The addition of the inventive oligomeric organosilanes and the addition of the fillers is preferably effected at mass temperatures of 100 to 200° C., but it can also be effected at a later stage at lower temperatures (40 to 100° C.), for example together with further rubber auxiliaries.

The oligomeric organosilanes can be added to the blending operation either in pure form or else applied to an inert organic or inorganic carrier. Preferred carrier materials are silicas, natural or synthetic silicates, aluminium oxide or carbon blacks.

Fillers used for the inventive rubber mixtures may be:
- carbon blacks: The carbon blacks for use here are produced by the lamp black, furnace black or gas black process and have BET surface areas of 20 to 200 m$^2$/g, for example SAF, ISAF, HSAF, HAF, FEF or GPF blacks. The carbon blacks may optionally also contain heteroatoms, for example Si.
- Silicas, preferably precipitated silicas, for example prepared by precipitation of solutions of silicates or flame hydrolysis of silicon halides having specific surface areas of 5 to 1000, preferably 20 to 400, m$^2$/g (BET surface area) and having primary particle sizes of 10 to 400 nm. The silicas may optionally also be in the form of mixed oxides with other metal oxides, such as Al oxides, Mg oxides, Ca oxides, Ba oxides, Zn oxides and titanium oxides.
- Synthetic silicates, such as aluminium silicate, alkaline earth metal silicates such as magnesium silicate or calcium silicate, having BET surface areas of 20 to 400 m$^2$/g and primary particle diameters of 10 to 400 nm.
- Natural silicates, such as kaolin and other naturally occurring silicas.
- Glass fibres and glass fibre products (mats, strands) and glass microbeads.

It is possible with preference to use carbon blacks having BET surface areas of 20 to 400 m$^2$/g or finely divided silicas prepared by precipitation of solutions of silicates, having BET surface areas of 20 to 400 m$^2$/g in amounts of 5 to 150 parts by weight, based in each case on 100 parts of rubber.

The fillers mentioned can be used alone or in a mixture. In a particularly preferred execution of the process, it is possible to use 10 to 150 parts by weight of light-coloured fillers, optionally together with 0 to 100 parts by weight of carbon black, and 0.3 to 10 parts by weight of an inventive oligomeric organosilane, based in each case on 100 parts by weight of rubber, for production of the mixtures.

For the production of inventive rubber mixtures, not only natural rubber but also synthetic rubbers are suitable. Preferred synthetic rubbers are described, for example, in W. Hofmann, Kautschuktechnologie [Rubber Technology], Genter Verlag, Stuttgart 1980. They include
- polybutadiene (BR)
- polyisoprene (IR)
- styrene/butadiene copolymers having styrene contents of 1 to 60%, preferably 2 to 50%, by weight (SBR)
- isobutylene/isoprene copolymers (IIR)
- butadiene/acrylonitrile copolymers having acrylonitrile contents of 5 to 60%, preferably 10 to 50%, by weight (NBR)
- partly hydrogenated or fully hydrogenated NBR rubber (HNBR)
- ethylene/propylene/diene copolymers (EPDM)

and mixtures of these rubbers. For the production of motor vehicle tyres, anionically polymerized L-SBR rubbers having a glass transition temperature above −50° C. in particular, and mixtures thereof with diene rubbers, are of interest.

The inventive rubber vulcanizates may comprise further rubber auxiliary products such as reaction accelerators, ageing stabilizers, thermal stabilizers, light stabilizers, antiozonants, processing auxiliaries, plasticizers, tackifiers, blowing agents, dyes, pigments, waxes, extenders, organic acids, retardants, metal oxides, and activators such as triethanolamine, polyethylene glycol, hexanetriol, which are known to the rubber industry.

The rubber auxiliaries are used in customary amounts guided by factors including the end use. Typical amounts are, for example, amounts of 0.1 to 50% by weight based on rubber. The oligomeric organosilanes can serve as crosslinkers alone. In general, it is advisable to add further crosslinkers. Further known crosslinkers used may be sulphur or peroxides. The inventive rubber mixtures may additionally comprise vulcanization accelerators. Examples of suitable vulcanization accelerators are mercaptobenzothiazoles, sulphenamides, guanidines, thiurams, dithiocarbamates, thioureas and thiocarbonates. The vulcanization accelerators and sulphur or peroxides can be used in amounts of 0.1 to 10% by weight, preferably 0.1 to 5% by weight, based on rubber.

The vulcanization of the inventive rubber mixtures can be effected at temperatures of 100 to 200° C., preferably 130 to 180° C., optionally under a pressure of 10 to 200 bar. The blending of the rubbers with the filler, any rubber auxiliaries and the inventive oligomeric organosilanes can be conducted in the customary mixing units, such as rollers, internal mixers and mixing extruders. The inventive rubber vulcanizates are suitable for production of shaped bodies. The inventive rubber mixtures can be used for production of tyres, profiles, cable sheaths, hoses, drive belts, conveyor belts, tyre covers, shoe soles, gasket rings and damping elements.

The invention further provides oligomeric organosilanes obtainable by the process according to the invention.

The inventive oligomeric organosilanes, in rubber mixtures, have the advantage of improved processibility and/or improved tear resistance.

The SH—(mercapto), S2—(disulphane), S3—(trisulphane), Sx—(polysulphane with x>3) distribution can be determined using $^1$H NMR spectroscopy, which is known to those skilled in the art.

The molar proportion of SiOEt and SiOR groups can be determined by $^{13}$C NMR spectroscopy, which is known to those skilled in the art.

In addition, the monomer content, and also M, D and T structures, can be determined using $^{29}$Si NMR spectrometry, which is likewise well known to the person skilled in the art.

Molar masses and the molar mass distribution can be determined by means of gel permeation chromatography (GPC). The GPC analysis method is described in detail in references including "Modern Size-Exclusion Liquid Chromatography", Andre Striegel et al., Wiley & Sons, 2nd ed. 2009. This involves using, as a standard for calibration of the method for siloxane analyses, a mixture of siloxanes of vinyltrimethoxysilane (vinyltrimethoxysilane, divinyltetramethoxydisiloxane, trivinylhexamethoxytrisiloxane, tetravinyloctamethoxytetrasiloxane). Columns used (MZ-Analysetechnik): Columns: 50×8.0 mm, MZ-Gel SDplus (styrene/divinylbenzene copolymer with high crosslinking level, spherical particle shape), porosity 50 A (angstroms, Å), 5 μm (micrometers) (pre-column), 300×8.0 mm, MZ-Gel SDplus, porosity 100 A (angstroms, Å), 5 μm, 300×8.0 mm, MZ-Gel SDplus, porosity 500 A (angstroms, Å), 5 μm; eluent and pump flow rate: methyl ethyl ketone (MEK) at 1 ml/min, standard substance: internal standard—1 g/1 ethylbenzene in 1% sample solution. The instrument is calibrated beforehand against a suitable substance (monomer, dimer, trisiloxane, etc.). Instrument (Agilent): 1100 Series isocratic pump G1310A, 1100 Series column oven G1316A, 1100 Series RID detector G1362A, manual injector G1328A, vacuum degasser G1322A, GPC software (PSS WinGPC Unity).

EXAMPLES

Octyltriethoxysilane, propyltriethoxysilane, Dynasylan® 9265 (phenyltriethoxysilane), Si 690® (bis(triethoxysilylpropyl) tetrasulphide) and VP Si 263® (3-mercaptopropyltriethoxysilane) are silanes from Evonik Industries.

Marlosol is a polyether alcohol of the formula HO—$(R^5$—$O)_m$—$R^6$ where $R^5$=$CH_2CH_2$, $R^6$=$C_{13}H_{27}$ and m=5 from Sasol.

Example 1

Preparation from VP Si 263®/octyltriethoxysilane/Marlosol (1:0.5:0.5)-0.8 eq $H_2O$.

A stirred apparatus is initially charged with VP Si 263® (417 g) and octyltriethoxysilane (242 g) and heated to 85° C. A mixture of $H_2O$ (38 g) and conc. HCl (0.3 g, 37%) in EtOH (363 g) is added dropwise and then the mixture is stirred for 8.5 h. After the oligomerization reaction has ended, the solvent and alcohol formed in the hydrolysis are removed under reduced pressure. Marlosol (368 g) and tetra-n-butyl titanate (0.5 g) are added and the reaction is heated to 140° C. for 1 h. The EtOH formed is removed by distillation under reduced pressure. The bottom product (793 g, 95% of theory) is a viscous orange liquid.

Density (20° C.): 1.012 g/cm$^3$
29Si NMR: 3% silane (VP Si 263®, octyltriethoxysilane), 49% M structures, 40% D structures, 9% T structures
GPC: Mn=967 g/mol, Mw=1234, Mz=1536, PDI=1.2761
Molar ratio of the alkyl polyether group —O—$(R^5$—$O)_m$—$R^6$ to silicon=0.33

Example 2

Preparation from VP Si 2630®/propyltriethoxysilane/Marlosol (1:0.5:0.5)-0.8 eq $H_2O$ A stirred apparatus is initially charged with VP Si 2630® (417 g) and propyltriethoxysilane (181 g) and heated to 85° C. A mixture of $H_2O$ (38 g) and conc. HCl (0.3 g, 37%) in EtOH (363 g) is added dropwise and then the mixture is stirred for 8 h. After the oligomerization reaction has ended, the solvent and alcohol formed in the hydrolysis are removed under reduced pressure. Marlosol (368 g) and tetra-n-butyl titanate (0.5 g) are added and the reaction is heated to 140° C. for 1 h. The EtOH formed is removed by distillation under reduced pressure. The bottom product (751 g, 94% of theory) is a viscous colourless liquid.

Density (20° C.): 1.029 g/cm$^3$
13C NMR: 78.6 mol % SiOEt, 21.4 mol % SiOR
29Si NMR: <1% silane (VP Si 263®, propyltriethoxysilane), 60% M structures, 35% D structures, 4% T structures
GPC: Mn=757 g/mol, Mw=1066, Mz=1417, PDI=1.4082
Molar ratio of the alkyl polyether group —O—$(R^5$—$O)_m$—$R^6$ to silicon=0.33

Example 3

Preparation from VP Si 263®/phenyltriethoxysilane (Dynasylan® 9265)/Marlosol (1:0.5:0.5)-0.8 eq $H_2O$ A stirred apparatus is initially charged with VP Si 263® (417 g) and Dynasylan® 9265 (210 g) and heated to 88° C. A mixture of $H_2O$ (38 g) and conc. HCl (0.3 g, 37%) in EtOH (363 g) is added dropwise and then the mixture is stirred for 6 h. After the oligomerization reaction has ended, the solvent and alcohol formed in the hydrolysis are removed under reduced pressure. Marlosol (368 g) and tetra-n-butyl titanate (0.5 g) are added and the reaction is heated to 140° C. for 1 h. The EtOH formed is removed by distillation under reduced pressure. The bottom product (797 g, 99% of theory) is a viscous, pale yellow liquid.

Density (20° C.): 1.050 g/cm$^3$
29Si NMR: 3% VP Si 263®, 1% Dynasylan® 9265, 51% M structures, 37% D structures, 8% T structures
GPC: Mn=770 g/mol, Mw=1013, Mz=1300, PDI=1.3156
Molar ratio of the alkyl polyether group —O—$(R^5$—$O)_m$—$R^6$ to silicon=0.33

Example 4

Inventive: Preparation from VP Si 263®/Si 69®/Marlosol (1:0.5:0.5)-0.8 eq $H_2O$ A stirred apparatus is initially charged with VP Si 263® (417 g) and Si 69® (466 g) and heated to 98° C. A mixture of $H_2O$ (38 g) and conc. HCl (0.3 g, 37%) in EtOH (363 g) is added dropwise and then the mixture is stirred for 8 h. After the oligomerization reaction has ended, the solvent and alcohol formed in the hydrolysis are removed under reduced pressure. Marlosol (368 g) and tetra-n-butyl titanate (0.5 g) are added and the reaction is heated to 140° C. for 1 h. The EtOH formed is removed by distillation under reduced pressure. The bottom product (1028 g, 98% of theory) is a viscous yellow liquid.

Density (20° C.): 1.082 g/cm$^3$
1H NMR: 40 mol % SH, 22 mol % S2, 27 mol % S3, 11 mol % Sx
13C NMR: 87.5 mol % SiOEt, 22.5 mol % SiOR
29Si NMR: 9% silane, 72% M structures, 19% D structures
GPC: Mn=1317 g/mol, Mw=5501, Mz=12291, PDI=4.1778
Molar ratio of the alkyl polyether group —O—$(R^5$—$O)_m$—$R^6$ to silicon=0.33

Comparative Example 5

Reference according to EP 0964021: Preparation from Si 69®/PTEO (1:5)-0.8 eq $H_2O$ A stirred apparatus is initially charged with Si 69® (240 g) and PTEO (464 g) and heated to 75° C. A mixture of $H_2O$ (45 g) and conc. HCl (0.5 g, 37%) in EtOH (436 g) is added dropwise and then the mixture is stirred for 12 h. After the oligomerization reaction has ended, the solvent and alcohol formed in the hydrolysis are removed under reduced pressure. The bottom product (518 g, >99% of theory) is a viscous yellow liquid.

29Si NMR: 0% silane PTEO, 0.4% silane Si 69®, 1% M structures of PTEO, 69% M structures of Si 69+D structures of PTEO, 28% D structures of Si 69®+T structures of PTEO, 1% T structures of Si 69®
GPC: Mn=871 g/mol, Mw=1473, Mz=2337, PDI=1.6916

Example 6

The formulation used for the rubber mixtures is specified in Table 1 below. In this table, the unit phr means parts by weight based on 100 parts by weight of the raw rubber used. The oligomeric silanes are used in isomolar amounts, based on the silane used in situ. The mixtures are prepared in a 1.5 l mixer (E type) at a batch temperature of 155° C.

TABLE 1

| Substance | Amount [phr] Ref. rubber mixture I "in situ" | Amount [phr] Ref. rubber mixture II, "in situ" | Amount [phr] Ref. rubber mixture III, comp. ex. 5 | Amount [phr] Inv. rubber mixture I, cont. inv. ex. 1 | Amount [phr] Inv. rubber mixture II, cont. inv. ex. 2 | Amount [phr] Inv. rubber mixture III, cont. inv. ex. 3 | Amount [phr] Inv. rubber mixture IV, cont. inv. ex. 4 |
|---|---|---|---|---|---|---|---|
| 1st stage | | | | | | | |
| Buna VSL 5025-2 | 96.25 | 96.25 | 96.25 | 96.25 | 96.25 | 96.25 | 96.25 |
| Buna CB 24 | 30 | 30 | 30 | 30 | 30 | 30 | 30 |
| Ultrasil 7000 GR | 80 | 80 | 80 | 80 | 80 | 80 | 80 |
| ZnO RS | 2 | 2 | 2 | 2 | 2 | 2 | 2 |
| Edenor ST1 | 1 | 1 | 1 | 1 | 1 | 1 | 1 |
| Vivatec 500 | 8.75 | 8.75 | 8.75 | 8.75 | 8.75 | 8.75 | 8.75 |
| Rhenogran DPG-80 | 2.5 | 2.5 | 2.5 | 2.5 | 2.5 | 2.5 | 2.5 |
| Protector G 3108 | 2 | 2 | 2 | 2 | 2 | 2 | 2 |
| Vulkanox-4020/LG | 2 | 2 | 2 | 2 | 2 | 2 | 2 |
| Vulkanox-HS/LG | 1.5 | 1.5 | 1.5 | 1.5 | 1.5 | 1.5 | 1.5 |
| Aktiplast ST | 3.5 | 3.5 | 3.5 | 3.5 | 3.5 | 3.5 | 3.5 |
| Si 69 ® | 6.4 | — | — | — | — | — | — |
| VP Si 363 ® | — | 10 | — | — | — | — | — |
| Reference silane according to comp. ex. 5 | — | — | 3.1 | — | — | — | — |
| Inv. silane according to ex. 1 | — | — | — | 6.0 | — | — | — |
| Inv. silane according to ex. 2 | — | — | — | — | 5.6 | — | — |
| Inv. silane according to ex. 3 | — | — | — | — | — | 5.8 | — |
| Inv. silane according to ex. 4 | — | — | — | — | — | — | 7.3 |
| 2nd stage | | | | | | | |
| Batch Stage 1 | | | | | | | |
| 3rd stage | | | | | | | |
| Batch Stage 2 | | | | | | | |
| Perkacit TBzTD | 0.2 | 0.2 | 0.2 | 0.2 | 0.2 | 0.2 | 0.2 |
| Vulkacit CZ/EG-C | 1.6 | 1.6 | 1.6 | 1.6 | 1.6 | 1.6 | 1.6 |
| Sulphur | 2.1 | 2.1 | 2.1 | 2.1 | 2.1 | 2.1 | 2.1 |

The polymer VSL 5025-2 is a solution-polymerized SBR copolymer from Bayer AG, having a styrene content of 25% by weight and a vinyl fraction of 50% by weight. The copolymer contains 37.5 phr TDAE oil and has a Mooney viscosity (ML 1+4/100° C.) of 47.

The polymer Buna CB 24 is a cis-1,4-polybutadiene (neodymium type) from Bayer AG, having a cis-1,4 content of at least 96% and a Mooney viscosity of 44±5.

Ultrasil 7000 GR is a readily dispersible silica from Evonik Industries AG and has a BET surface area of 170 $m^2/g$.

The TDAE oil used is Vivatec 500 from Klaus Dahleke KG, Vulkanox 4020 is 6PPD from Lanxess Europe GmbH & Co. KG, Vulkanox HS/LG is TMQ from Lanxess and Protektor G3108 is an antiozonant wax from Paramelt B.V.; ZnO RS is ZnO from Arnsperger Chemikalien GmbH; EDENOR ST1 GS 2.0 is palmitic/stearic acid from Caldic Deutschland GmbH & Co. KG; Aktiplast ST is a plasticizer from RheinChemie, which consists of a blend of hydrocarbons, zinc soaps and fillers. Rhenogran DPG-80 consists of 80% DPG on an EVA/EPDM carrier from RheinChemie, and Vulkacit CZ is CBS from Lanxess Europe GmbH & Co. KG. Perkacit TBzTD (tetrabenzylthiuram disulphide) is a product from Flexsys N.V.

The rubber mixture is produced in three stages in an internal mixer according to Table 2.

TABLE 2

| Stage 1 | |
|---|---|
| Settings | |
| Mixing unit | Werner & Pfleiderer GK 1.5E |
| Speed | 80 min$^{-1}$ |
| Ram pressure | 5.5 bar |
| Flow temp. | 80° C. |
| Mixing process | |
| 0 to 0.5 min | Buna VSL 5025-1 + Buna CB 24 |
| 0.5 min | TMQ, 6PPD |
| 0.5 bis 1 min | mix |
| 1 to 2 min | ½ Ultrasil 7000 GR, silane or oligomeric organosilanes, ZnO |
| 2 min | clean and ventilate |
| 2 to 3 min | ½ Ultrasil 7000 GR, Protector G3108, stearic acid, Vivatec 500, DPG, plasticizer |
| 3 min | clean and ventilate |
| 3 to 4 min | mix and discharge at 150-160° C. |
| Stage 2 | |
| Settings | |
| Mixing unit | as in stage 1 except: |
| Speed | 90 min$^{-1}$ |
| Mixing process | |
| 0 to 1 min | break up stage 1 batch |
| 1 to 3 min | mix at 155° C. |
| 3 min | discharge |

TABLE 2-continued

| Stage 3 | |
|---|---|
| Settings | |
| Mixing unit | as in stage 1 except |
| Speed | 40 min$^{-1}$ |
| Flow temp. | 50° C. |
| Mixing process | |
| 0 to 0.5 min | stage 2 batch |
| 0.5 to 2 min | accelerator and sulphur |
| 2 min | discharge and form milled sheet on laboratory roll mill (diameter 200 mm, length 450 mm, flow temperature 50° C.) Homogenize: form a milled sheet with roll gap 3-4 mm for 20 s, and within a further 40 s: cut and fold over 3* to the left, 3* to the right and roll 3* with a narrow roll gap (3 mm) and then draw off a milled sheet. |
| Batch temp. | <110° C. |

The general process for producing rubber mixtures and vulcanizates thereof is described in "Rubber Technology Handbook", W. Hofmann, Hanser Verlag 1994.

The rubber testing is effected by the test methods specified in Table 3.

TABLE 3

| Physical testing | Standard/conditions |
|---|---|
| Moving die method: minimum torque | DIN 53529/3, ISO 6502 |
| Ring tensile test, 23° C. | DIN 53504, ISO 37 |
| Stress values | |
| DIN abrasion | DIN ISO 4649, ISO 4649 |
| Shore hardness | DIN 53505, ISO 7619-1 |
| Tear resistance, die C | ASTM D 624 |
| Ball rebound, 70° C. | ASTM D 2632 |
| Viscoelastic properties | DIN 53 513, ISO 2856 |
| 0 and 60° C., 16 Hz, initial force 50 N and amplitude force 25 N | |
| Complex modulus E* (MPa) | |

The vulcanization is effected at a temperature of 165° C. for a period of 15 minutes. Table 4 reports the rubber data for raw mixture and vulcanizate.

TABLE 4

| Substance | Ref. rubber mixture I "in situ" | Ref. rubber mixture II, "in situ" | Ref. rubber mixture III, comp. ex. 5 | Inv. rubber mixture I, cont. inv. ex. 1 | Inv. rubber mixture II, cont. inv. ex. 2 | Inv. rubber mixture III, cont. inv. ex. 3 | Inv. rubber mixture IV, cont. inv. ex. 4 |
|---|---|---|---|---|---|---|---|
| Crude mixture results: | | | | | | | |
| Moving die method: minimum torque after 3rd stage [dNm] | 2.3 | 2.9 | 2.1 | 2.7 | 2.1 | 1.9 | |
| Vulcanizate results: | | | | | | | |
| 50% stress value [mPa] | 1.2 | 1.05 | 1.15 | 1.2 | 1.1 | 1.1 | |
| 200% stress value [mPa] | 7.2 | 4.8 | 8.9 | 9.2 | 8.3 | 7.6 | |

TABLE 4-continued

| Substance | Ref. rubber mixture I "in situ" | Ref. rubber mixture II, "in situ" | Ref. rubber mixture III, comp. ex. 5 | Inv. rubber mixture I, cont. inv. ex. 1 | Inv. rubber mixture II, cont. inv. ex. 2 | Inv. rubber mixture III, cont. inv. ex. 3 | Inv. rubber mixture IV, cont. inv. ex. 4 |
|---|---|---|---|---|---|---|---|
| Strengthening index: 200%/50% stress value [—] | 6.0 | | 4.6 | 7.7 | 7.7 | 7.5 | 6.9 |
| DIN abrasion [mm³] | 95 | 105 | 104 | 67 | 61 | 69 | 72 |
| Shore hardness | 60 | 55 | 60 | 56 | 58 | 55 | 58 |
| Ball rebound, 70° C. [%] | 65.0 | 68.8 | 63.0 | 72.1 | 71.6 | 70.8 | 70.1 |
| Tear resistance, die C [N/mm] | 40.2 | 49 | 33.4 | 36.7 | 44.4 | 40.7 | 37.5 |
| MTS, 16 Hz, initial force 50 N, ampl. force 25 N, 0° C. [MPa] | 0.454 | 0.412 | 0.476 | 0.449 | 0.478 | 0.462 | 0.474 |
| MTS, 16 Hz, initial force 50 N, ampl. force 25 N, 60° C. [MPa] | 0.109 | 0.108 | 0.130 | 0.087 | 0.093 | 0.093 | 0.096 |

The rubber mixtures containing the inventive oligomeric silanes show improved processing characteristics (lower torque after the 3rd mixing stage), improved strengthening characteristics (higher moduli and better reinforcement index), improved rolling resistance and improved tear resistance compared to the isomolar in situ mixture or the oligomeric silane according to EP 0964021.

The invention claimed is:

1. An oligomeric organosilane, comprising structural unit A and at least one structural unit selected from structural units B, C and D joined in a linear, branched or cyclic arrangement;

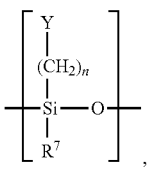   A

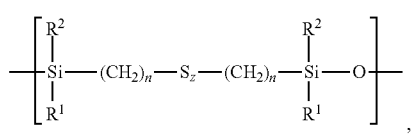   B

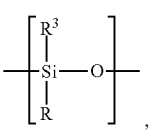   C

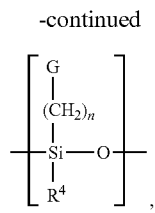   D wherein:

Y represents H, F, Cl, Br, I, SCN, SH, $-S_x-(CH_2)_n SiRR^1R^2$ or $-N(R^8)_2$;

$R^8$ independently represents H, $(C_1-C_{16})$ alkyl, $-(CH_2)_2NH_2$, $-(CH_2)_2NH-(CH_2)_2NH_2$ or $-(CH_2)_2N[(CH_2)_2 NH_2]_2$;

n represents 1-8;

G represents H, F, Cl, Br, I, SCN, SH, $-S_x-(CH_2)_n SiRR^1R^2$ or $-N(R^8)_2$, such that G is different from Y;

R, $R^1$, $R^2$, $R^3$, $R^4$, each independently represent OH, $(C_1-C_{16})$alkyl, $(C_2-C_{16})$alkenyl, $(C_6-C_{14})$aryl, $(C_1-C_4)$ alkoxy, an $OSiR^1R^2R^3$ group or an alkyl polyether group $-O-(R^5-O)_m-R^6$;

$R^5$ independently represents a branched or unbranched, saturated or unsaturated, aliphatic divalent C1-C30 hydrocarbon group;

m on average is 1 to 30;

$R^6$ represents an unsubstituted or substituted, branched or unbranched $C_1-C_{30}$ alkyl group, $C_2-C_{30}$ alkenyl group, a $C_6-C_{14}$ aryl group, or a $C_7-C_{40}$ aralkyl group;

$R^7$ represents an alkyl polyether group $-O-(R^5-O)_m-R^6$;

x on statistical average is 1-6; and z on statistical average is 1-6.

2. The oligomeric organosilane of claim 1, wherein an molecular weight of the oligomeric organosilane is between 400 and 100,000 g/mol.

3. The oligomeric organosilane of claim 1, wherein:
the oligomeric organosilane comprises the structural units A and B and C; and
$R^7$ represents the alkyl polyether group —O—$(R^5$—O$)_m$—$R^6$.

4. The oligomeric organosilane of claim 3, wherein;
in structural unit A,
   n represents 3, and
   Y represents SH;
in structural unit B,
   $R^1$ represents ethoxy or alkyl polyether group —O—$(R^5$—O$)_m$—$R^6$,
   $R^2$ represents ethoxy or alkyl polyether group —O—$(R^5$—O$)_m$—$R^6$,
   n represents 3, and
   z represents 2-4; and
in structural unit C,
   R represents phenyl, propyl or octyl, and
   $R^3$ represents ethoxy or alkyl polyether group —O—$(R^5$—O$)_m$—$R^6$.

5. The oligomeric organosilane of claim 1, wherein:
the oligomeric organosilane comprises the structural units A and B; and
$R^7$ represents the alkyl polyether group —O—$(R^5$—O$)_m$—$R^6$.

6. The oligomeric organosilane of 5, wherein:
in structural unit A,
   n represents 3, and
   Y represents SH; and
in structural unit B,
   $R^1$ represents ethoxy or alkyl polyether group —O—$(R^5$—O$)_m$—$R^6$,
   $R^2$ represents ethoxy or alkyl polyether group —O—$(R^5$—O$)_m$—$R^6$,
   n represents 3, and
   z represents 2-4.

7. The oligomeric organosilane of claim 1, wherein:
the oligomeric organosilane comprises the structural units A and D; and
$R^7$ represents the alkyl polyether group —O—$(R^5$—O$)_m$—$R^6$.

8. The oligomeric organosilane of claim 7, wherein:
in structural unit A,
   n represents 3, and
   Y represents SH; and
in structural unit D,
   G represents Cl or $NH_2$,
   n represents 3, and
   $R^4$ represents ethoxy or alkyl polyether group —O—$(R^5$—O$)_m$—$R^6$.

9. The oligomeric organosilane of claim 1, wherein:
the oligomeric organosilane comprises the structural units A and C and D,
$R^7$ represents the alkyl polyether group —O—$(R^5$—O$)_m$—$R^6$.

10. The oligomeric organosilane of claim 9, wherein:
in structural unit A,
   n represents 3, and
   Y represents SH;
in structural unit C,
   R represents phenyl, propyl or octyl, and
   $R^3$ represents ethoxy or alkyl polyether group —O—$(R^5$—O$)_m$—$R^6$; and
in structural unit D,
   G represents Cl or $NH_2$,
   $R^4$ represents ethoxy or alkyl polyether group —O—$(R^5$—O$)_m$—$R^6$, and
   n represents 3.

11. The oligomeric organosilane of claim 1, wherein:
the oligomeric organosilane comprises the structural units A and C; and
$R^7$ represents the alkyl polyether group —O—$(R^5$—O$)_m$—$R^6$.

12. The oligomeric organosilane of claim 11, wherein:
in structural unit A,
   n represents 3, and
   Y represents SH; and
in structural unit C,
   R represents phenyl, propyl or octyl, and
   $R^3$ represents ethoxy or alkyl polyether group —O—$(R^5$—O$)_m$—$R^6$.

13. A process for preparing the oligomeric organosilane of claim 1, the process comprising:
oligomerizing/polymerizing the compound of formula I and at least one of the compounds of formulae II-IV:

$$\begin{array}{c} Y \\ | \\ (CH_2)_n \\ | \\ R^9 - Si - R^9 \\ | \\ R^7 \end{array} \quad \text{I}$$

$$R^9 - \underset{\underset{R^1}{|}}{\overset{\overset{R^2}{|}}{Si}} - (CH_2)_n - S_z - (CH_2)_n - \underset{\underset{R^1}{|}}{\overset{\overset{R^2}{|}}{Si}} - R^9 \quad \text{II}$$

$$\begin{array}{c} R^3 \\ | \\ R^9 - Si - R^9 \\ | \\ R \end{array} \quad \text{III}$$

$$\begin{array}{c} G \\ | \\ (CH_2)_n \\ | \\ R^9 - Si - R^9 \\ | \\ R^4 \end{array} \quad \text{IV}$$

in the presence of water at temperatures of 0-150° C., to form an intermediate; and
reacting the intermediate with an alkyl polyether alcohol of formula HO—$(R^5$—O$)_m$—$R^6$, to form the oligomeric organosilane,
wherein:
Y, G, R, $R^1$, $R^2$, $R^3$, $R^4$, $R^5$, $R^6$, $R^7$, $R^8$, n, m, u, x and z are each as defined in claim 1; and
$R^9$ independently represents H, F, Cl, Br, I, or $(C_1$-$C_{16})$ alkoxy.

14. The process of claim 13, wherein the oligomerizing/polymerizing, the reacting, or both, occurs in the presence of a catalyst.

15. The process of claim 14, wherein:
the oligomerizing/polymerizing occurs in the present of HCl as catalyst; and
the reacting occurs in the present of tetrabutyl orthotitanate as catalyst.

16. The process of claim 13, wherein the oligomerizing/polymerizing, the reacting, or both, occurs in the presence of a solvent which is ethyl acetate or ethanol.

17. A rubber mixture, comprising the oligomeric organosilane of claim 1.

18. A tire, profile, cable sheath, hose, drive belt, conveyor belt, tyre cover, shoe sole, gasket ring or damping element comprising the rubber mixture of claim 17.

19. An oligomeric organosilane obtained by the process of claim 13.

20. An oligomeric organosilane, comprising structural unit D and at least one structural unit selected from structural units A, B and C, joined in a linear, branched or cyclic arrangement:

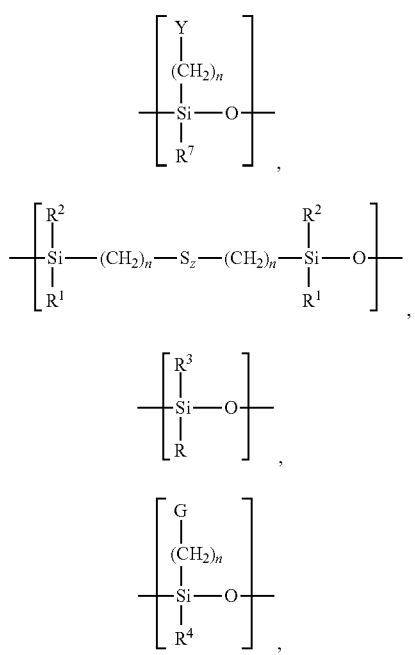

wherein:
Y represents H, F, Cl, Br, I, SCN, SH, —$S_x$—$(CH_2)_n$ $SiRR^1R^2$ or —$N(R^8)_2$;
$R^8$ independently represents H, ($C_1$-$C_{16}$) alkyl, —$(CH_2)_2$ $NH_2$, —$(CH_2)_2NH$—$(CH_2)_2NH_2$ or —$(CH_2)_2N$ $[(CH_2)_2 NH_2]_2$;
n represents 1-8;
G represents H, F, Cl, Br, I, SCN, SH, —$S_x$—$(CH_2)_n$ $SiRR^1R^2$ or —$N(R^8)_2$, such that G is different from Y;
R, $R^1$, $R^2$, $R^3$, $R^4$, $R^7$ each independently represent OH, ($C_1$-$C_{16}$)alkyl, ($C_2$-$C_{16}$)alkenyl, ($C_6$-$C_{14}$)aryl, ($C_1$-$C_4$) alkoxy, an $OSiR^1R^2R^3$ group or an alkyl polyether group —O—$(R^5$—O$)_m$—$R^6$;

$R^5$ independently represents a branched or unbranched, saturated or unsaturated, aliphatic divalent C1-C30 hydrocarbon group;
m on average is 1 to 30;
$R^6$ represents an unsubstituted or substituted, branched or unbranched $C_1$-$C_{30}$ alkyl group, $C_2$-$C_{30}$ alkenyl group, a $C_6$-$C_{14}$ aryl group, or a $C_7$-$C_{40}$ aralkyl group;
x on statistical average is 1-6;
z on statistical average is 1-6; and
at least one R, $R^1$, $R^2$, $R^3$, $R^4$ or $R^7$ group is an alkyl polyether group —O—$(R^5$—O$)_m$—$R^6$.

21. A process for preparing the oligomeric organosilane of claim 20, the process comprising:
oligomerizing/polymerizing the compound of formula IV and at least one of the compounds of formulae I-III:

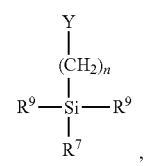

I

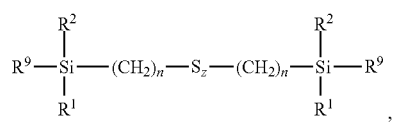

II

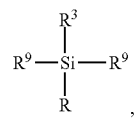

III

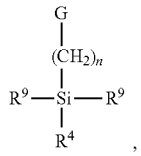

IV in the presence of water at temperatures of 0-150° C., to form an intermediate; and
reacting the intermediate with an alkyl polyether alcohol of formula HO—$(R^5$—O$)_m$—$R^6$, to form the oligomeric organosilane,
wherein:
Y, G, R, $R^1$, $R^2$, $R^3$, $R^4$, $R^5$, $R^6$, $R^7$, $R^8$, n, m, u, x and z are each as defined in claim 20; and
$R^9$ independently represents H, F, Cl, Br, I, or ($C_1$-$C_{16}$) alkoxy.

* * * * *